United States Patent
Sander

(10) Patent No.: US 6,975,451 B2
(45) Date of Patent: Dec. 13, 2005

(54) ILLUMINATION INCOUPLING SYSTEM FOR AN OPTICAL VIEWING DEVICE

(75) Inventor: Ulrich Sander, Rebstein (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 0 days.

(21) Appl. No.: 10/374,913

(22) Filed: Feb. 26, 2003

(65) Prior Publication Data

US 2003/0161037 A1 Aug. 28, 2003

(30) Foreign Application Priority Data

Feb. 27, 2002 (DE) .............. 102 08 594

(51) Int. Cl.⁷ .......... G02B 21/06; G02B 21/00
(52) U.S. Cl. ............ 359/389; 359/368; 359/375; 359/385
(58) Field of Search ............ 359/368–390, 359/431, 857–861, 831–837; 351/200–247

(56) References Cited

U.S. PATENT DOCUMENTS

| | | | |
|---|---|---|---|
| 4,674,845 A * | 6/1987 | Matsumura | 359/377 |
| 4,991,947 A * | 2/1991 | Sander et al. | 359/375 |
| 5,126,877 A * | 6/1992 | Biber | 359/389 |
| 5,760,952 A * | 6/1998 | Koetke | 359/389 |
| 5,856,883 A | 1/1999 | Sander | 359/389 |
| 5,898,518 A | 4/1999 | Biber | 359/385 |
| 6,011,647 A | 1/2000 | Geschwentner | 359/389 |
| 6,563,113 B1 | 5/2003 | Amann et al. | 250/309 |

FOREIGN PATENT DOCUMENTS

| | | | |
|---|---|---|---|
| DE | 33 27 672 | 2/1985 | |
| DE | 4331635 | 6/1994 | |
| DE | 19650773 | 7/1997 | |
| EP | 0661020 | 7/1995 | |
| JP | 57-6823 | * 1/1982 | ......... 359/386 |
| WO | 95 294 19 | 11/1995 | |
| WO | 99 133 70 | 3/1999 | |

* cited by examiner

*Primary Examiner*—Thong Q Nguyen
(74) *Attorney, Agent, or Firm*—Davidson, Davidson & Kappel, LLC

(57) ABSTRACT

In an illumination incoupling system for an optical viewing device, illumination incoupling is provided simultaneously into main observer beam paths and assistant observer beam paths using two semitransparent and two fully reflective deflection elements arranged crosswise and symmetrically with respect to the optical axis of the main objective. Homogeneous illumination of the specimen field may thereby be achieved for both the main observer and the assistant observer.

15 Claims, 5 Drawing Sheets

ILLUMINATION INCOUPLING SYSTEM FOR AN OPTICAL VIEWING DEVICE

CROSS REFERENCE TO RELATED APPLICATIONS

This application claims priority to German patent application DE 102 08 594.3, which is hereby incorporated by reference herein.

BACKGROUND

The invention concerns an illumination incoupling system for an optical viewing device, for example for a surgical microscope.

BACKGROUND

In known illumination devices for surgical microscopes having two or four observer channels (see European patent document EP-A1-661 020, German patent document DE-A1-43 31 635, and German patent document DE-A1-196 50 773), two deflection elements are used to reflect the illuminating ray bundle into the observer beam paths. They are arranged symmetrically with respect to the main observation beam paths, thereby resulting in an asymmetry in the assistant observer beam paths (see, e.g., FIG. 2 in German patent document DE-A1-43 31 635). The illumination devices described have, in practice, the following disadvantages in terms of the red reflection:
  a) The main observer and the assistant observer, who actually should be seeing the same thing, receive different red reflections.
  b) Since the illuminating mirrors are arranged on only one side, "rolling" of a patient's eye in its socket can modify the red reflection of both observers.

SUMMARY OF THE INVENTION

It is thus an object of the present invention to provide an illumination incoupling system that divides the illuminating ray bundle, and couples it into the observer beam paths, in such a way that the assistant observer always sees the same red reflections as the main observer.

The present invention provides an illumination incoupling system for an optical viewing device, in particular for a surgical stereomicroscope having main observer beam paths (3a, b) and assistant observer beam paths (4a, b), wherein in the operating state, two illuminating ray bundles having axes (1a, b) are provided that are each divided, by deflection elements (7a, b and 8a, b) arranged symmetrically with respect to the optical axis (5) of the main objective (6), into two illuminating ray bundles having axes (2a, b), the illuminating light being reflected simultaneously into the main observer beam paths (3a, b) and into the assistant observer beam paths (4a, b).

In addition to the previously known deflection elements that have been described, two deflection elements arranged crosswise and symmetrically with respect to the optical axis of the main objective are used on the axes of the illuminating ray bundles in an embodiment of the present invention. The deflection elements previously known are configured here to be semitransparent and/or—according to a development—to be fully reflective in specific zones. The additional deflection elements according to the present invention are fully reflective. Complete symmetry of the illumination incoupling system in relation to the observer beam paths of the surgeon and the assistant is thus created. The assistant observer now receives, in the assistant observer beam path, a red reflection equivalent in quality to that of the main observer; and the observer also receives a good red reflection if the patient's eye "rolls" as mentioned above. The disadvantages are therefore compensated for by the crosswise and symmetrical arrangement, according to the present invention, of the deflection elements.

In order to achieve a further improvement with this assemblage, the two additional deflection elements according to the present invention can be arranged in swing-out and/or radially displaceable fashion, and/or can be equipped with a shutter. This eliminates disadvantages that in some circumstances can have a disruptive effect if, during viewing of the patient's eye in the first-named arrangement according to the present invention, the four reflected images reflect on the cornea.

The illumination incoupling system according to the present invention, having two additional symmetrically arranged deflection elements, yields the following improvements:

Because of the symmetrical arrangement of the incoupled illuminating ray bundles, the assistant observer receives the same red reflection as the main observer.

If the patient's eye "rolls," the main observer and the assistant observer continue to see the same red reflection.

The illumination pupil is not geometrically divided, but rather guided via the semitransparent deflection elements, in the context of a physical light division, onto a second pair of deflection elements. Light distribution in the specimen field is thereby more homogeneous.

Because of the physical light division, the overall height of the system is kept much lower. Further improvements according to the present invention include the following:

Undesired reflections can be eliminated by way of the shutters and the ability of the deflection elements to swing out.

The radial displaceability of the deflection elements allows the observer to configure the red reflections in accordance with his wishes.

The external shape of the deflection elements may be adapted to the respective contour of the ray bundle cross section of the observer beam paths.

The text above refers to a surgical microscope, but the present invention is not limited thereto; it is instead also usable in other optical devices having an illumination incoupling system, e.g., projectors and illumination systems for video and photographic cameras, in which the red reflection is of no significance but comparable problems can occur when reflecting in light.

When the "axis of a ray bundle" is mentioned below, the correlated illuminating ray bundle associated therewith is also meant thereby.

BRIEF DESCRIPTION OF THE DRAWINGS

The present invention will be illuminated upon in greater detail below with reference to the drawings.

DETAILED DESCRIPTION

Figure 1:
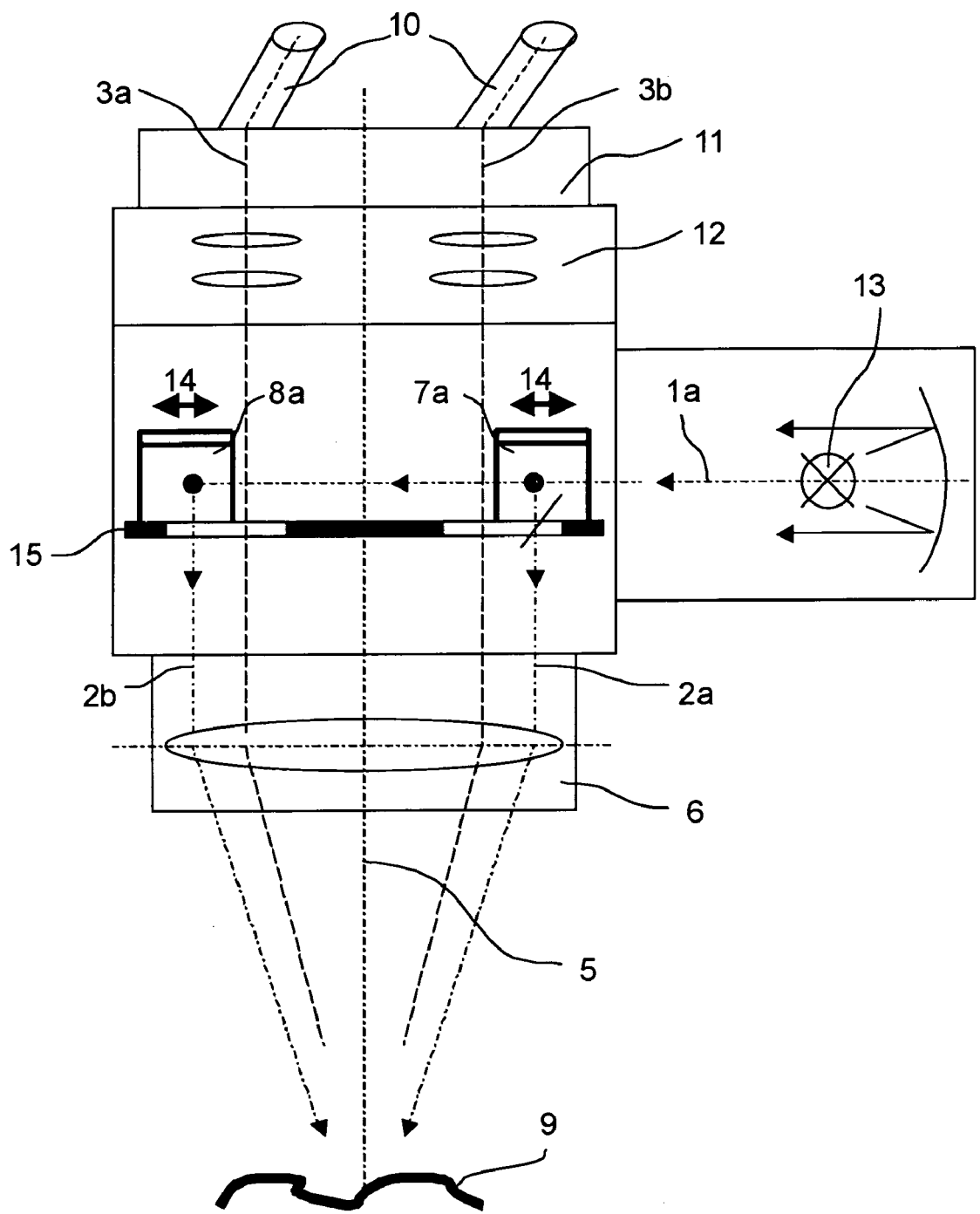
FIG. 1 shows a side view of a surgical stereomicroscope having an optical incoupling system according to an embodiment of the present invention.

FIG. 1 shows, in a side view, a surgical stereomicroscope having an optical axis 5 of the main objective 6; having eyepieces 10, a tube 11, a zoom 12; having observer beam paths 3a, b and a light source 13. A portion of the ray bundle generated by light source 13, with its axis 1a, is deflected at semitransparent deflection element 7a to an axis 2a. The light of the illuminating ray bundle that passes through is deflected at a fully reflective deflection element 8a (for example a mirror or a prism) parallel to a further axis 2b.

The ray bundles correlated with the two axes 2a, b, produced from ray bundle 1a after division and deflection at deflection elements 7a and 8a, illuminate a specimen field 9 through a main objective 6. The two radially-displaceable deflection elements 7a and 8a, indicated by double arrows 14, are located on one horizontal plane, e.g., at axis 1a. Shutter 15 is provided for selectably darkening at least one of deflection elements 7a and 8a.

Figure 2:
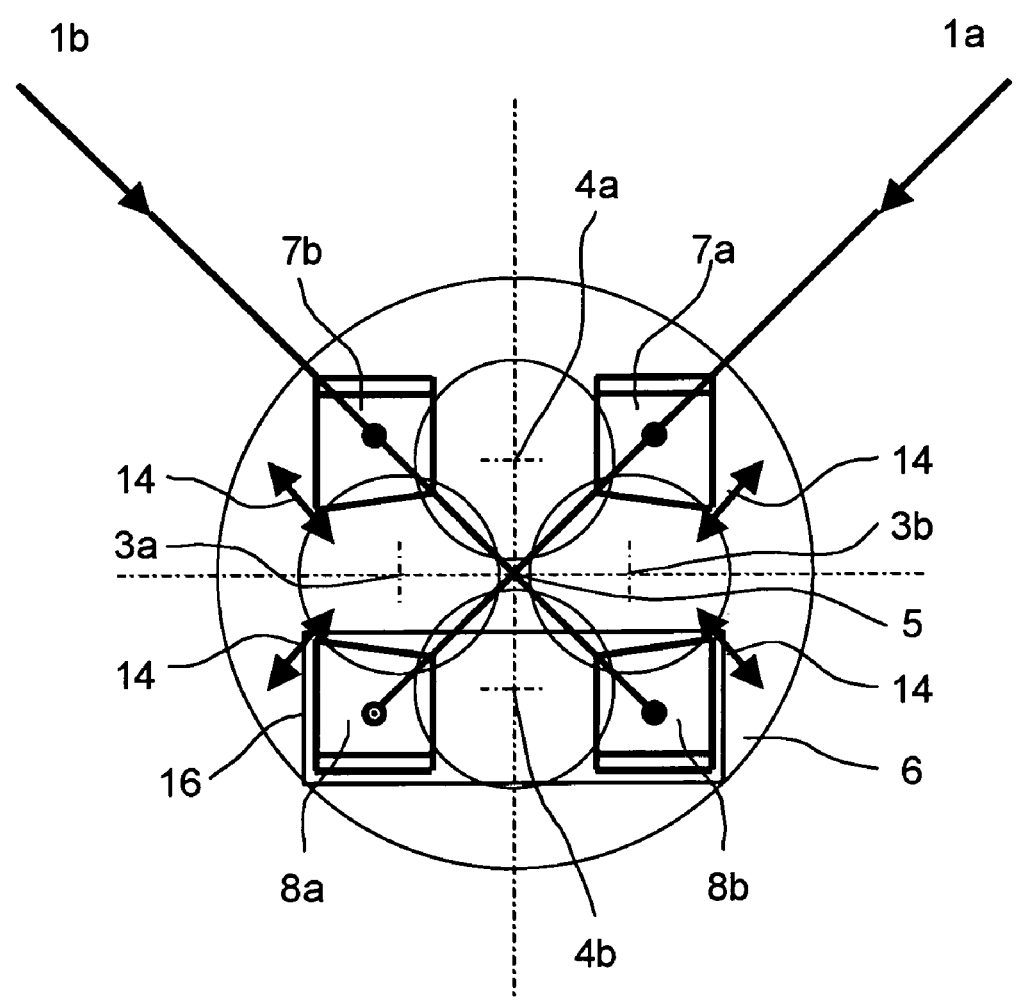
FIG. 2 shows a plan view of the optical incoupling system of the surgical stereomicroscope shown in FIG. 1.

FIG. 2 shows, in a plan view, the configuration of the illumination incoupling system, with axis 1a of the illuminating ray bundle, that has already been depicted in side view in FIG. 1. Axis 1b arranged in mirror-image fashion with respect to axis 1a and deflection elements 7a and 8a, and deflection elements 7b and 8b, are depicted. Observer beam paths 3a, b and assistant observer beam paths 4a, b are visible in plan view.

In this embodiment, axes 1a and 1b of the illuminating ray bundles intersect optical axis 5 of main objective 6. Deflection elements 7a, 8a and 7b, 8b are arranged in a same horizontal plane, e.g., defined by axes 1a and 1b of the illuminating ray bundles. Additionally evident is the arrangement of deflection elements 7a, 8a and 7b, 8b in rotationally symmetrical fashion with respect to optical axis 5. Deflection elements 8a and 8b are integrated in a single device 16.

The illuminating ray bundles having axes 1a, b are respectively reflected at semitransparent deflection elements 7a, b into observer beam paths 3b, a, respectively, and into the one assistant observer beam path 4a. The illuminating ray bundles having axes 1a, b that pass through deflection elements 7a, b are respectively coupled at fully reflective deflection elements 8a, b into observer beam paths 3a, b, respectively, and into the second observer beam path 4b. The arrangement of deflection elements 7a, b and 8a, b crosswise and symmetrically with respect to optical axis 5 of main objective 6 results in homogeneous illumination of specimen field 9 both for observer beam paths 3a, b and for assistant observer beam paths 4a, b.

Figure 3:
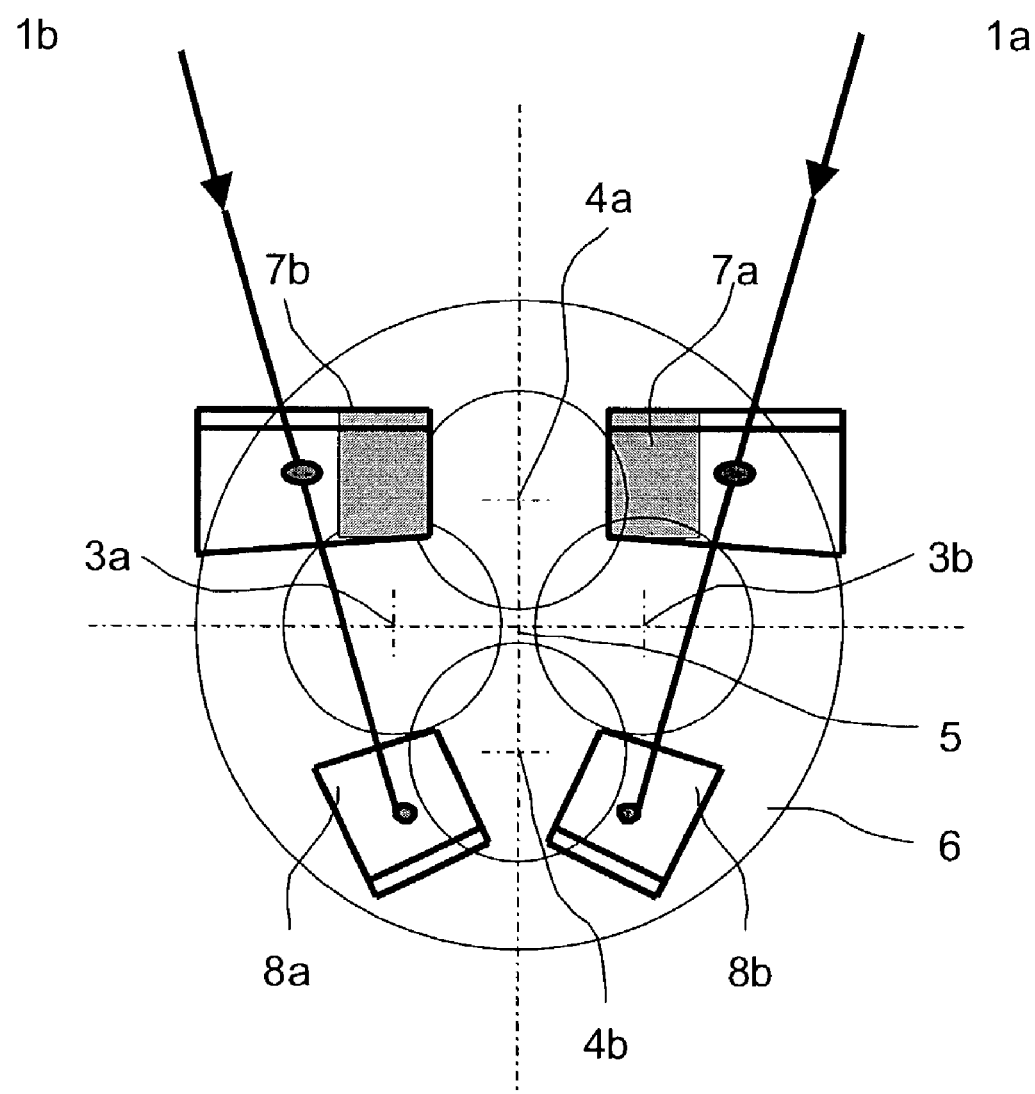
FIG. 3 shows a plan view of a second embodiment of an optical incoupling system according to the present invention for the surgical stereomicroscope shown in FIG. 1.

FIG. 3 shows, as a variant of the configuration shown in FIG. 2, a configuration in which the intersection point of axes 1a, b of the illuminating beam paths deviates from optical axis 5 of main objective 6, and deflection elements 7a, b are divided into several zones (indicated by cross-hatching). These zones are configured to be transparent and/or semitransparent and/or fully reflective. This makes possible, in specific zones, unimpeded transmission of the illuminating ray bundles having axes 1a, b onto additional deflection elements 8a, b according to the present invention. Largely homogeneous illumination over specimen field 9 is thereby once again achieved.

Figure 4:
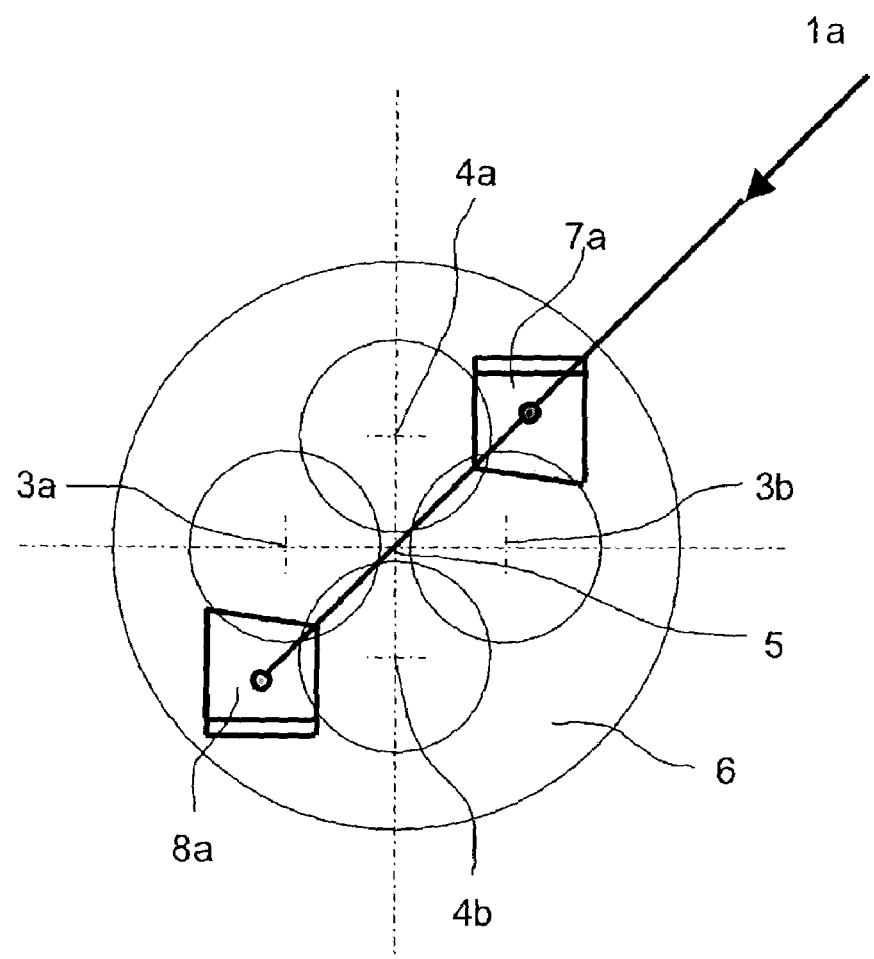
FIG. 4 shows a plan view of a third embodiment of an optical incoupling system according to the present invention for the surgical stereomicroscope shown in FIG. 1 using a single illuminating ray bundle.

FIG. 4 shows a variant of the configuration shown in FIG. 2 in which only a single illuminating ray bundle 1a is used. As a result, the corneal reflections (red reflection) can again be reduced even though the illumination of observer beam paths 3a, b and assistant observer beam paths 4a, b is uniform, and the physical design is further simplified.

Figure 5:
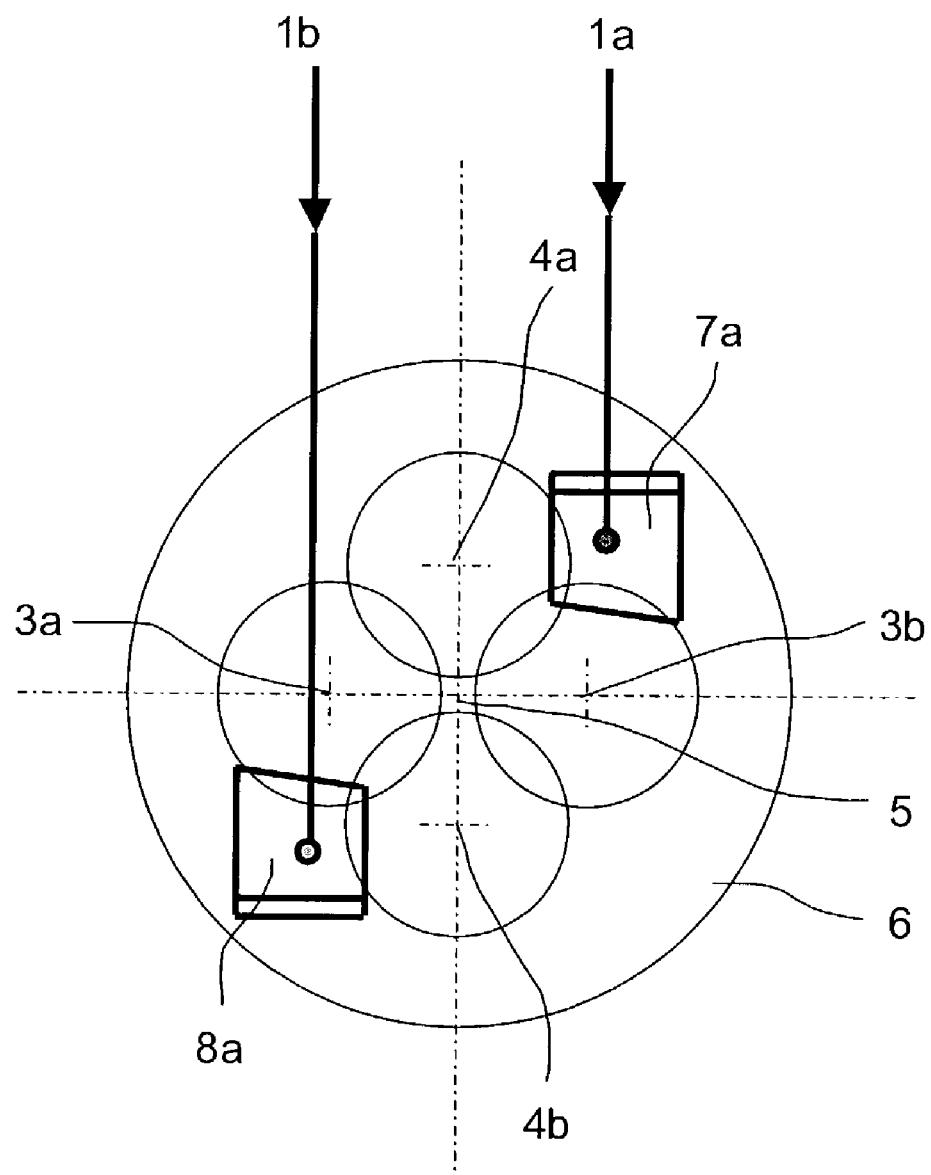
FIG. 5 shows a plan view of a fourth embodiment of an optical incoupling system according to the present invention for the surgical stereomicroscope shown in FIG. 1 using two parallel illuminating ray bundles.

FIG. 5 shows a variant of the configuration shown in FIGS. 2 and 4 in which two parallel illuminating ray bundles, with their axes 1a, b, are used. These are deflected at deflection elements 7a, 8a, which in this variant embodiment are of fully reflective configuration. The result once again is homogeneous illumination over specimen field 9 and a physically simple design.

In cases in which two illumination axes are utilized, these can be used with two separate light sources or with only one light source and appropriate additional splitter elements.

What is claimed is:

1. An illumination incoupling system for an optical viewing device, comprising:
    a first deflection element; and
    a second deflection element;
wherein the second deflection element is disposed after the first deflection element on a first illuminating beam axis, and the first and second deflection elements are symmetrically disposed with respect to an optical axis of a main objective of the optical viewing device and configured, in an operating state, to simultaneously reflect illuminating light having the first illuminating beam axis into a main observer beam path and an assistant observer beam path.

2. The illumination incoupling system as recited in claim 1 wherein the optical viewing device is a surgical stereomicroscope.

3. The illumination incoupling system as recited in claim 1 further comprising a third deflection element and a fourth deflection element symmetrically disposed with respect to the optical axis of the main objective, the first, second, third and fourth deflection elements forming a crosswise arrangement about the optical axis of the main objective, and wherein the first and third deflection elements each include a respective semitransparent deflection device and the second and fourth deflection elements each include a respective fully reflective deflection devices, the fourth deflection element being disposed after the third deflection element on a second illuminating beam axis.

4. The illumination incoupling system as recited in claim 3 wherein the first, second, third and fourth deflection elements are disposed in a same horizontal plane.

5. The illumination incoupling system as recited in claim 1 wherein the first and second deflection elements are disposed in a same horizontal plane.

6. The illumination incoupling system as recited in claim 1 wherein at least one of the first and second deflection elements includes a respective deflection mirror.

7. The illumination incoupling system as recited in claim 1 wherein at least one of the first and second deflection elements includes a respective deflection prism.

8. The illumination incoupling system as recited in claim 1 further comprising a third deflection element and a fourth deflection element symmetrically disposed with respect to the optical axis of the main objective, the first, second, third and fourth deflection element forming a crosswise arrangement about the optical axis of the main objective, and wherein the first and second deflection elements are configured to reflect light of a first illuminating ray bundle having the first illuminating beam axis and the third and fourth deflection elements are configured to reflect light of a second illuminating ray bundle having a second illuminating beam axis, the first and second illuminating beam axes intersecting at the optical axis of the main objective.

9. The illumination incoupling system as recited in claim 1 further comprising a third deflection element and a fourth deflection element symmetrically disposed with respect to the optical axis of the main objective, and wherein the fourth deflection element is disposed after the third deflection element on a second illuminating beam axis, and wherein the first and third deflection elements each include at least one of a respective semitransparent deflection mirror and a respective semitransparent deflection prism.

10. The illumination incoupling system as recited in claim 1 further comprising a third deflection element and a fourth deflection element symmetrically disposed with respect to the optical axis of the main objective, the fourth deflection element being disposed after the third deflection element on a second illuminating beam axis, and wherein the second and fourth deflection elements each include at least one of a respective fully reflective deflection mirror and a respective fully reflective deflection prism.

11. The illumination incoupling system as recited in claim 1 further comprising a shutter configured to selectably darken at least one of the first and second deflection elements.

12. The illumination incoupling system as recited in claim 1 wherein the second deflection element is displaceable so as to achieve different illumination angles of a specimen field.

13. The illumination incoupling system as recited in claim 1 further comprising a third deflection element and a fourth deflection element symmetrically disposed with respect to the optical axis of the main objective, the fourth deflection element being disposed after the third deflection element on a second illuminating beam axis, and wherein the second and fourth deflection elements are integrated in a single device.

14. The illumination incoupling system as recited in claim 1 wherein a respective external shape of at least one of the first and second deflection elements is adapted to a respective contour of a ray bundle cross section of at least one of the main observer and the assistant observer beam paths.

15. An illumination incoupling system for an optical viewing device, comprising:
    a first deflection element;
    a second deflection element;
    a third deflection element; and
    a fourth deflection element;
wherein:
    the first and third deflection elements are symmetrically disposed with respect to an optical axis of a main objective of the optical viewing device and configured, in an operating state, to simultaneously reflect illuminating light into a main observer beam path and an assistant observer beam path;
    the first and third deflection elements each include a respective semitransparent deflection device and the second and fourth deflection elements each include a respective fully reflective deflection devices; and
    the second and fourth deflection elements are movably disposed so as to be slidable or swingable between a first position and a second position, the second and fourth deflection elements being symmetrically disposed with respect to the optical axis of the main objective in the first position so as to form, with the first and third deflection elements, a crosswise arrangement about the optical axis of the main objective, the second deflection element being disposed, in the first position, after the first deflection element on a first illuminating beam axis, the fourth deflection element being disposed, in the first position, after the third deflection element on a second illuminating beam axis, the second deflection element being disposed off of the first illuminating beam axis in the second position and the fourth deflection element being disposed off of the second illuminating beam axis in the second position.

* * * * *